(12) United States Patent
Kurdyumov

(10) Patent No.: US 9,410,044 B2
(45) Date of Patent: Aug. 9, 2016

(54) BORON-CONTAINING LINKING AGENTS

(71) Applicant: SurModics, Inc., Eden Prairie, MN (US)

(72) Inventor: Aleksey V. Kurdyumov, Maplewood, MN (US)

(73) Assignee: SurModics, Inc., Eden Prairie, MN (US)

( * ) Notice: Subject to any disclaimer, the term of this patent is extended or adjusted under 35 U.S.C. 154(b) by 608 days.

(21) Appl. No.: 13/886,031

(22) Filed: May 2, 2013

(65) Prior Publication Data

US 2013/0302529 A1  Nov. 14, 2013

Related U.S. Application Data

(60) Provisional application No. 61/645,903, filed on May 11, 2012.

(51) Int. Cl.
| | |
|---|---|
| *C07F 5/02* | (2006.01) |
| *C09D 5/00* | (2006.01) |
| *C08J 7/12* | (2006.01) |
| *C08J 7/18* | (2006.01) |
| *C07F 5/00* | (2006.01) |

(52) U.S. Cl.
CPC . *C09D 5/00* (2013.01); *C07F 5/003* (2013.01); *C07F 5/02* (2013.01); *C07F 5/022* (2013.01); *C07F 5/025* (2013.01); *C08J 7/123* (2013.01); *C08J 7/18* (2013.01)

(58) Field of Classification Search
None
See application file for complete search history.

(56) References Cited

U.S. PATENT DOCUMENTS

| | | | |
|---|---|---|---|
| 5,002,582 A | 3/1991 | Guire et al. | |
| 6,465,525 B1 | 10/2002 | Guire et al. | |
| 2009/0093550 A1 | 4/2009 | Rolfes et al. | |
| 2010/0190966 A1* | 7/2010 | Lin | C07K 16/18 530/391.1 |

OTHER PUBLICATIONS

Kroschwitz, , "Plastics", Concise Encyclopedia of Polymer Science and Engineering, p. 462-464, 1990 (4 pages).

* cited by examiner

*Primary Examiner* — Ramsey Zacharia
(74) *Attorney, Agent, or Firm* — Pauly, De Vries Smith & Deffner, L.L.C.

(57) ABSTRACT

Embodiments of the invention include linking agents including borate, borazine, or boronate groups and coatings and devices that incorporate such linking agents, along with related methods. Other embodiments are also included herein.

7 Claims, No Drawings

BORON-CONTAINING LINKING AGENTS

This application claims the benefit of U.S. Provisional Application No. 61/645,903, filed May 11, 2012, the contents of which are herein incorporated by reference.

FIELD OF THE INVENTION

The present invention relates to linking agents. More specifically, the present invention relates to linking agent compounds containing boron atoms, and coatings and devices that incorporate such linking agents, along with related methods.

BACKGROUND OF THE INVENTION

Photochemically reactive functional groups ("photoreactive groups" or "photogroups") are functional groups that, when exposed to an appropriate energy source, undergo a transformation from an inactive state (i.e., ground state) to a reactive intermediate capable of forming covalent bonds with appropriate materials. Photoreactive groups can be used, for instance, to derivatize a target molecule (e.g., thermochemically), in order to then photochemically attach the derivatized target molecule to a surface. Photoreactive groups can also be used as photoinitiators for polymerization reactions.

SUMMARY OF THE INVENTION

Embodiments of the invention include linking agents including borate, borazine, or boronate groups and coatings and devices that incorporate such linking agents, along with related methods. In an embodiment, the invention includes a compound having the structure (I):

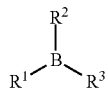

(I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

In an embodiment, the invention includes a device including a substrate; a linking agent having the structure (I) shown above, wherein $R^1$ is a radical comprising a photoreactive group; $R^2$ is selected from OH, a radical comprising a photoreactive group, an alkyl group and an aryl group; and $R^3$ is selected from OH, a radical comprising a photoreactive group, alkyl group and aryl group; the linking agent bound to the surface of the substrate through the residue of at least one photoreactive group.

In an embodiment, the invention includes a device comprising a substrate; a linking agent having the structure (I) shown above wherein $R^1$ is a radical comprising a photoreactive group; $R^2$ is selected from OH, a radical comprising a photoreactive group, and alkyl group and an aryl group; and $R^3$ is selected from OH, a radical comprising a photoreactive group, an alkyl group and an aryl group; the linking agent bound to the surface of the substrate through the residue of at least one photoreactive group; and a desired compound disposed on the substrate, the desired compound selected from the group consisting of monomers, macromers, and polymers, the desired compound bound to the linking agent through the residue of at least one photoreactive group on the linking agent.

In an embodiment, the invention includes a method of coating a surface of a substrate, the method comprising the steps of providing a photoreactive linking agent capable, upon activation, of covalent attachment to the surface of the substrate, the agent having the structure (I) shown above wherein $R^1$ is a radical comprising a photoreactive group; $R^2$ is selected from OH, a radical comprising a photoreactive group, an alkyl group and an aryl group; and $R^3$ is selected from OH, a radical comprising a photoreactive group, an alkyl group and an aryl group; forming a coating composition comprising the linking agent and a solvent system; placing the coating composition in bonding proximity to the surface of the substrate, and activating the photoreactive groups of the linking agent in order to bond the photoreactive linking agent to the surface.

In an embodiment, the invention includes a method of coating a surface of a substrate, the method including the steps of providing a photoreactive linking agent capable, upon activation, of covalent attachment to the surface of the substrate, the agent having the structure (I) shown above wherein $R^1$ is a radical comprising a photoreactive group; $R^2$ is selected from OH, a radical comprising a photoreactive group, an alkyl group and an aryl group; and $R^3$ is selected from OH, a radical comprising a photoreactive group, an alkyl group and an aryl group; forming a coating composition comprising the linking agent, a polymer, and a solvent system; depositing the coating composition on the surface of the substrate, and activating the photoreactive groups of the linking agent in order to bond the polymer to the surface.

In yet other embodiments, the linking agent can include a photo group (or photoreactive group) and a borazine group. An exemplary structure for embodiments with linking agents having a borazine group include structure (II):

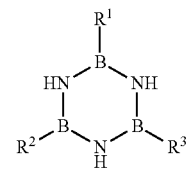

(II)

wherein $R^1$ is a radical comprising a photoreactive group; $R^2$ is selected from OH, a radical comprising a photoreactive group, an alkyl group, a halide and an aryl group; and $R^3$ is selected from OH, a radical comprising a photoreactive group, an alkyl group, a halide and an aryl group. In some embodiments the bonds B—$R^1$, B—$R^2$ and B—$R^3$ can be chosen independently to be interrupted by a heteroatom, such as O, N, S, or mixtures thereof.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Embodiments herein can include linking agents and devices, including but not limited to medical devices that incorporate such linking agents, along with related methods. Linking agents of the present invention can be used to immobilize (e.g., by cross-linking) otherwise nonreactive molecules to a surface and/or to each other. Linking agents of the present invention can also be used to prepare a primed latent reactive surface, which can be used for the later application of a target molecule.

As used herein, the term "water soluble" shall refer to a linking agent having sufficient solubility to allow it to be effectively used under aqueous conditions.

In various embodiments, the linking agent can include a photo group (or photoreactive group) and a borate or boronate group. For example, embodiments of linking agents can include a linking agent having the structure:

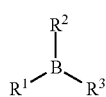

(I)

wherein $R^1$ is a radical comprising a photoreactive group; $R^2$ is selected from OH, a radical comprising a photoreactive group, an alkyl group and an aryl group; and $R^3$ is selected from OH, a radical comprising a photoreactive group, an alkyl group and an aryl group. In some embodiments the bonds B—$R^1$, B—$R^2$ and B—$R^3$ can be chosen independently to be interrupted by a heteroatom, such as O, N, S, or mixtures thereof.

In yet other embodiments, the linking agent can include a photo group (or photoreactive group) and a borazine group. An exemplary structure for embodiments with linking agents having a borazine group include structure (II):

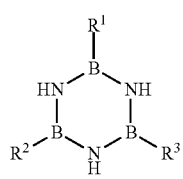

(II)

wherein $R^1$ is a radical comprising a photoreactive group; $R^2$ is selected from OH, a radical comprising a photoreactive group, an alkyl group, a halide and an aryl group; and $R^3$ is selected from OH, a radical comprising a photoreactive group, an alkyl group, a halide and an aryl group. In some embodiments the bonds B—$R^1$, B—$R^2$ and B—$R^3$ can be chosen independently to be interrupted by a heteroatom, such as O, N, S, or mixtures thereof.

As used herein, the term "photoreactive group" refers to a molecule or portion thereof having one or more functional groups that are capable of responding to a specific applied external stimulus to undergo active specie generation and form a covalent bond with an adjacent chemical structure, which can be provided by the same or a different molecule. Photoreactive groups are those groups of atoms in a molecule that retain their covalent bonds unchanged under conditions of storage but that, upon activation by an external energy source, form one or more covalent bonds with other molecules. In one embodiment, the photoreactive groups can generate active species such as free radicals upon absorption of electromagnetic energy. Photoreactive groups can be chosen to be responsive to various portions of the electromagnetic spectrum, including, for example, the ultraviolet and visible portions of the spectrum. Photoreactive groups are described, for example, in U.S. Pat. No. 5,002,582, the disclosure of which is incorporated herein by reference.

In various embodiments, the photoreactive group includes a photoreactive aryl ketone, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. One example includes thioxanthone, and its derivatives, having excitation energies greater than about 360 nm. In one embodiment, the photoreactive group is a functionalized benzophenone with an amine or hydroxyl substituent at positions 3 or 4 (i.e., 3- or 4-aminobenzophenone or 3- or 4-hydroxybenzophenone). As discussed above, the functionalized benzophenone can include a linker between the benzophenone photoreactive group and the amine or hydroxyl substituent. Examples of linkers include an amine, an ether, linear or branched $C_1$-$C_{10}$ alkyl, or a combination thereof.

The functional groups of such ketones are readily capable of undergoing the activation/inactivation/reactivation cycle described herein. Benzophenone is one example of a photoreactive moiety that is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are subject to multiple reactivation in water and may increase coating efficiency.

The azides constitute one class of photoreactive groups and include derivatives based on arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides (RO)$_2$PON$_3$ such as diphenyl phosphoryl azide and diethyl phosphoryl azide. Diazo compounds constitute another class of photoreactive groups and include derivatives of diazoalkanes (—$CHN_2$) such as diazomethane and diphenyldiazomethane, diazoketones (—CO—CHN$_2$) such as diazoacetophenone and 1-trifluoromethyl-1-diazo-2-pentanone, diazoacetates (—O—CO—CHN$_2$) such as t-butyl diazoacetate and phenyl diazoacetate, and beta-keto-alpha-diazoacetates (—CO—CN$_2$—CO—O—) such as t-butyl alpha diazoacetoacetate. Other photoreactive groups include the diazirines (—CHN$_2$) such as 3-trifluoromethyl-3-phenyldiazirine, and ketenes (—CH=C=O) such as ketene and diphenylketene.

Exemplary photoreactive groups, and their residues upon activation, are shown as follows.

| Photoreactive Group | Residue |
|---|---|
| aryl azides | amine (R—NH—R') |
| acyl azides | amide (R—CO—NH—R') |
| azidoformates | carbamate (R—O—CO—NH—R') |
| sulfonyl azides | sulfonamide (R—SO$_2$—NH—R') |
| phosphoryl azides | phosphoramide ((RO)$_2$PO—NH—R') |
| diazoalkanes | new C—C bond |
| diazoketones | new C—C bond and ketone |
| diazoacetates | new C—C bond and ester |
| beta-keto-alpha-diazoacetates | new C—C bond and beta-ketoester |
| aliphatic azo | new C—C bond |
| diazirines | new C—C bond |
| ketenes | new C—C bond |
| photoactivated ketones | new C—C bond and alcohol |

Photoinitiation of free radicals can take place via various mechanisms, including photochemical intramolecular photocleavage, hydrogen abstraction, and redox reactions. In one embodiment, photoinitiation takes place by hydrogen abstraction from the polymerizable groups.

Intramolecular photocleavage involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone. For example, in one embodiment wherein the linking agent is provided in the form of a quinone having adjacent carbonyl groups (e.g., camphorquinone), photoinitiation takes place via intramolecular bond cleavage.

A second mechanism, hydrogen abstraction, can be either intra- or intermolecular in nature. A system employing this mechanism can be used without additional energy transfer acceptor molecules and by nonspecific hydrogen abstraction. However, this system is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone and camphorquinone.

A third mechanism involves photosensitization reactions utilizing photoreducible or photo-oxidizable dyes. In most instances, photoreducible dyes are used in conjunction with a reductant, typically a tertiary amine. The reductant intercepts the induced triplet producing the radical anion of the dye and the radical cation of the reductant.

In one embodiment, photoinitiation generates active species such as free radicals, including nitrenes, carbenes, and excited states of ketones upon absorption of electromagnetic energy. This excited photoinitiator in turn abstracts hydrogen atoms from available sources in proximity to the photoinitiator, e.g., polymerizable species. This hydrogen abstraction thus generates a free radical site within the polymerizable species from which polymerization can proceed.

In various embodiments, the linking agent is water soluble. By way of example, in various embodiments, the linking agent has a water solubility of at least about 0.1 mg/ml (at 25° Celsius and neutral pH). In some embodiments, the linking agent has a water solubility of at least about 0.5 mg/ml (at 25° Celsius and neutral pH). In some embodiments, the linking agent has a water solubility of at least about 1.0 mg/ml (at 25° Celsius and neutral pH).

In other embodiments, the linking agent is water insoluble. For example, in some embodiments, the linking agent has a water solubility of less than about 0.1 mg/mL (at 25° Celsius and neutral pH). In some embodiments, the linking agent has a water solubility of less than about 0.01 mg/mL (at 25° Celsius and neutral pH).

Preparation of Linking Agents

Linking agents of the present invention can be prepared using available reagents and chemical conversions within the skill of those in the relevant art.

The following reaction diagram illustrates a one step process for formation of a borate compound in accordance with an embodiment herein. This diagram illustrates that the borate compound can be formed according to the reaction between a compound including a photoreactive group and a suitable reactive group, such as a terminal alcohol, and boric acid. A further example of this is shown in Example 1 below.

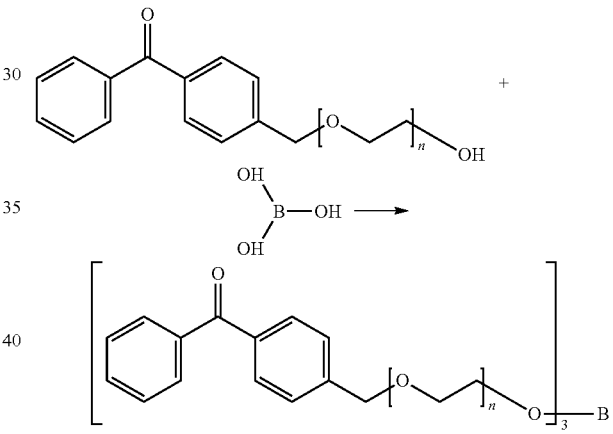

Similarly, a general process for formation of the linking group containing a borazine group can be performed. For example, 2,4,6-trihydroxy borazine can be reacted with a photoreactive group having a suitable reactive group, such as a terminal alcohol. Additionally, a linking group containing a borazine group can alternatively be formed by reacting 2,4,6-trichloro borazine with a photoreactive group having a suitable reactive group, such as a terminal alcohol. The resulting general structure is:

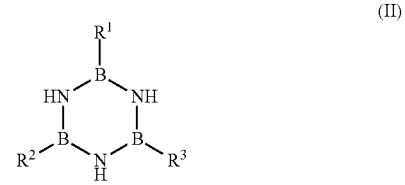

(II)

wherein $R^1$ is a radical comprising a photoreactive group; $R^2$ is a radical comprising a photoreactive group; and $R^3$ is a radical comprising a photoreactive group.

Compounds having photoreactive group and a suitable reactive group, such as a terminal alcohol, can be formed in various ways. An example of this type of process is disclosed at least in example 3 of U.S. Pat. No. 6,465,525, the content of which is herein incorporated by reference.

It will be appreciated that borate and boronate compounds herein can be complexed with other compounds. By way of example, borate compounds can be complexed with compounds including amine groups, including but not limited to secondary amines.

Further Applications

Linking agents included herein can be usefully applied in various applications. By way of example, in some embodiments, such linking agents can be used in order to prime the surfaces of a substrate. In some embodiments, such linking agents can be used in order to bond polymers to the surfaces of substrate. In some embodiments, linking agents herein can be used in order to form a coating on the surface of a substrate. In some embodiments, such linking agents can be used in order to cross-link polymers.

In one embodiment, the linking agent described herein is applied to a surface having carbon-hydrogen bonds with which the photoreactive groups can react to immobilize the linking agents. In one embodiment, the support surface provides abstractable hydrogen atoms suitable for covalent bonding with the activated group. In another embodiment, the surface can be modified (e.g., by pretreatment with a suitable reagent) to provide abstractable hydrogen atoms on the surface.

In an embodiment, the invention includes a method of priming a surface of a substrate. The method can include steps of providing a photoreactive linking agent capable, upon activation, of covalent attachment to the surface of the substrate, the agent comprising a photoreactive group and a borate or boronate group. The method can further include forming a coating composition comprising the linking agent and a solvent system. The solvent system can include one or more solvents. The method can further include placing the coating composition in bonding proximity to the surface of the substrate. The method can further include activating the photoreactive groups of the linking agent in order to bond the photoreactive linking agent to the surface.

In one embodiment, the degradable linking agent is used to form a coating on a substrate surface. In one embodiment, the coating is hydrophobic. In another embodiment, the coating is hydrophilic. The coating can be formed in any suitable manner, e.g., by simultaneous or sequential attachment of the linking agent and a compound or agent to be bonded (or "desired compound") to a support surface.

In some embodiments, the method involves simultaneous application of a linking agent and a compound or agent to be bonded (or "desired compound"), in the same solution or in two separate solutions, to a substrate followed by activation of the photoreactive groups in the linking agent. The compound to be bonded can include various components, both polymeric and non-polymeric. In some embodiments, the agent to be bonded can be selected from the group consisting of monomers, macromers, and polymers.

The method of coating a surface of a substrate can include providing a photoreactive linking agent capable, upon activation, of covalent attachment to the surface of the substrate, the agent comprising a photoreactive group and a borate or boronate group. The method further includes forming a coating composition comprising the linking agent, a polymer, and a solvent system. The solvent system can include one or more solvents. It will be appreciated that many different solvents can be used depending on the solubility properties of the particular linking agent used and the agent to be bonded. In some embodiments, the solvent system can be aqueous. In some embodiments, the solvent system can include water and a co-solvent, such as isopropanol. In some embodiments, the solvent system includes at least 50 percent isopropanol by volume.

The method can also include depositing the coating composition on the surface of the substrate. This can be accomplished in any suitable manner. Various techniques can be used including dip coating, spray coating (ultrasonic or gas atomization), brush coating, knife coating, roller coating, and the like.

The method can also include activating the photoreactive groups of the linking agent in order to bond the desired compound to the surface. Activation can be achieved in various ways. For example, the solution can be illuminated in situ to activate the photoreactive group(s) that serve as a photoinitiator(s), thus initiating attachment via hydrogen abstraction. Specifically, the surface can be illuminated with UV light of the appropriate wavelength, thereby activating the photoreactive groups on the linking agent. The linking agent is thus immobilized to the surface, by means of the photoreactive group. Simultaneously, the desired compound is bonded to the linking agent through another of the photoreactive groups. In some embodiments, activation takes place in an inert atmosphere. Deoxygenation can take place using an inert gas such as nitrogen.

In some embodiments, activation is carried out after application of the coating composition to the substrate, but before the coating composition dries (e.g., before the solvent evaporates off). In other embodiments, activation is carried out after application of the coating composition to the substrate and after the coating composition dries.

Substrates

It will be appreciated that the method described herein is suitable for use in connection with a variety of support surfaces, including hydrogel polymers, silicone, polypropylene, polystyrene, poly(vinyl chloride), polycarbonate, poly(methyl methacrylate), parylene and any of the numerous organosilanes used to pretreat glass or other inorganic surfaces. The photoreactive linking agents can be applied to surfaces in any suitable manner (e.g., in solution or by dispersion), then photoactivated by uniform illumination to immobilize them to the surface. Examples of suitable hydrogel polymers are selected from silicone hydrogels, hydroxyethylmethacrylate polymers, and glyceryl methacrylate polymers.

Other suitable surface materials include polyolefins, polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. See generally, "Plastics," pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymer layer. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

Compounds to be Bonded

In various embodiments the linking agent is used to bond a desired compound to the surface of a substrate. In some embodiments, the desired compound can include one or more polymerizable groups. In accordance with such an embodiment, the photoreactive group serves as an initiator to initiate polymerization of the polymerizable groups. As used herein, "polymerizable group" refers to a group that is adapted to be polymerized by initiation via free radical generation, and by photoinitiators activated by visible or long wavelength ultraviolet radiation.

A variety of desired compounds are suitable for use as with the linking agent described herein. In one embodiment, the desired compound is hydrophilic or is capable of being modified to provide hydrophilic characteristics at appropriate reaction conditions (e.g., pH). Desired compounds to be bonded can include polymers and non-polymers. In some embodiments, desired compounds are selected from monomeric polymerizable molecules (e.g., monomers), and macromeric polymerizable molecules (e.g., macromers), and polymers. As used herein, "macromer" shall refer to a macromolecular monomer having a molecular weight of about 250 to about 25,000, and from about 1,000 to about 5,000.

Suitable desired compounds can contain electrically neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate).

Alternatively, suitable desired compounds containing electrically neutral hydrophilic functional units include molecules whose polymers, once formed, can be readily modified (e.g., hydrolyzed by the addition of ethylene oxide) to provide products with enhanced affinity for water. Examples of suitable monomers of this type include glycidyl acrylate or methacrylate, whose polymers bear epoxy groups that can be readily hydrolyzed to provide glycol structures having a high affinity for water.

Examples of suitable monomeric desired compounds that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric desired compounds that are negatively charged at appropriate pH levels include molecules whose polymers, once formed, can be readily modified (e.g., by hydrolysis via the addition of ethylene oxide) to provide products with enhanced affinity for water. Examples of suitable monomers of this type include maleic anhydride, whose polymers bear anyhdride groups that can be readily hydrolyzed to provide carboxylic acid groups, or can be readily reacted with amines to provide amide/acid structures with high affinity for water, and polymerized vinyl esters.

Examples of suitable monomeric desired compounds that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric desired compounds include those molecules that can be readily modified (e.g., by hydrolysis via the addition of ethylene oxide) to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In an alternative embodiment, the desired compounds include macromeric polymerizable molecules. Suitable macromers can be synthesized from monomers such as those illustrated above. Examples of suitable macromeric polymerizable compounds include methacrylate derivatives, monoacrylate derivatives, and acrylamide derivatives. Macromeric polymerizable compounds include poly(ethylene glycol)monomethyacrylate, methoxypoly(ethylene glycol) monomethacrylate, poly(ethylene glycol)monoacrylate, monomethyacrylamidopoly(acrylamide), poly(acrylamide-co-3-methacrylamidopropylacrylamide), poly(vinylalcohol) monomethacrylate, poly(vinylalcohol)monoacrylate, poly (vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer.

Poly(ethylene glycol) of a desired molecular weight can be synthesized or purchased from a commercial source, and modified (e.g., by reaction with methacrylyl chloride or methacrylic anhydride) to introduce the terminal methacrylate ester units to produce a suitable macromer. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

In one embodiment, the degradable linking agent is used to form a coating on a substrate surface. In one embodiment, the coating is hydrophobic. In another embodiment, the coating is hydrophilic. The coating can be formed in any suitable manner, e.g., by simultaneous or sequential attachment of the linking agent and chemical compounds (e.g., molecules bearing polymerizable groups) to a support surface. In one embodiment, the method involves a two step process, involving sequential steps in which linking agent is first attached to the surface, after which compounds are polymerized thereon using the photoinitator of the attached agent. One advantage of a sequential approach is that photopolymerization of this sort allows the generation of thin polymer layers on the support surface. The resultant polymer layer is typically highly adherent, uniform in thickness, and is highly durable. Moreover, solutions used to form the polymer layer can be applied (e.g., via in solution application, dip coating, spray coating, knife coating, and roller coating) to any suitable support surface of any surface morphology. The resultant polymer layer, in turn, can be adapted to cover irregular surfaces as well as smooth, relatively uniform surfaces. The polymerizable species can also be attached to the support surface simultaneously with the linking agent, by providing suitable reaction conditions to allow such simultaneous attachment of the linking agent and polymerization of the polymerizable species.

The photoinitiator group (i.e., the second photoreactive group, or latent reactive group) can be identical to, or different from, the first photoreactive group used to attach the linking agent to a support surface. In one embodiment, the first and second photoreactive groups are adapted to be independently activated by light of different wavelengths (e.g., ultraviolet light versus visible light).

Upon activation of the photoreactive groups in the presence of a support surface, the second photoreactive group(s) remain unbound to the support surface and revert to their inactive state (e.g., latent) in order to serve as photoinitiator groups. While not intending to be bound by theory, it appears that the ability of a photoreactive group to remain unbound (and hence serve as a photoinitiator) is a factor, at least in part, of various reaction conditions (e.g., time and intensity of illumination wavelength, reagent concentration, etc.) and/or restrictions imposed by the size and/or structure of the linking agent itself. The photoinitiator thus remains available to be subsequently activated by a suitable energy source, and thereby initiate photopolymerization.

In one embodiment, the linking agent described herein is applied to a surface having carbon-hydrogen bonds with which the photoreactive groups can react to immobilize the linking agents. In one embodiment, the support surface provides abstractable hydrogen atoms suitable for covalent bonding with the activated group. In another embodiment, the surface can be modified (e.g., by pretreatment with a suitable reagent) to provide abstractable hydrogen atoms on the surface.

The method described herein is suitable for use in connection with a variety of support surfaces, including hydrogel polymers, silicone, polypropylene, polystyrene, poly(vinyl chloride), polycarbonate, poly(methyl methacrylate), parylene and any of the numerous organosilanes used to pretreat glass or other inorganic surfaces. The photoreactive linking agents can be applied to surfaces in any suitable manner (e.g., in solution or by dispersion), then photoactivated by uniform illumination to immobilize them to the surface. Examples of suitable hydrogel polymers are selected from silicone hydrogels, hydroxyethylmethacrylate polymers, and glyceryl methacrylate polymers.

Other suitable surface materials include polyolefins, polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. See generally, "Plastics," pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymer layer. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

Surface modification can be achieved using photopolymerization (e.g., by free radical polymerization). In accordance with the present method, a selected surface is contacted with a linking agent, as described above. During and/or after application of the linking agent, the surface is illuminated with UV light of the appropriate wavelength, thereby activating the photoreactive groups. The linking agent is thus immobilized to the surface, by means of the first photoreactive groups (with the second photoreactive groups reverting to inactive form), and excess linking agent can then be optionally washed away, leaving a surface primed with a base layer of linking agent.

The linking agent can be applied to the surface of interest in any suitable manner. For example, the linking agent can be applied by dip coating or by dispersing the agent on the surface (for example, by spray coating). Suitable methods of application include application in solution, dip coating, spray coating, knife coating, and roller coating. In one embodiment, the linking agent is applied to the surface via spray coating, as this application method provides increased density of the linking agent on the support surface, thereby improving grafting durability.

In the sequential approach described herein, a solution containing polymerizable compounds can be applied to a primed surface. The solution can be illuminated in situ to activate the second photoreactive group(s) that serve as a photoinitiator(s), thus initiating free radical polymerization via hydrogen abstraction. In one embodiment, photopolymerization takes place in an inert atmosphere, since oxygen interferes with free radical polymerization. Deoxygenation can take place using an inert gas such as nitrogen.

Once the system has been deoxygenated, the surface can again be illuminated with UV light of the appropriate wavelength. This second illumination thus activates the second photoreactive group(s) serving as a photoinitiator(s) of free radical polymerization. In one embodiment, illumination generates the excited state of the photoreactive group, allowing the excited molecule to abstract a hydrogen from available sources, e.g., molecules bearing polymerizable groups. Such hydrogen abstraction generates a free radical site, from which polymerization can proceed.

The method includes steps of providing a support surface and applying a linking agent to the support surface. In one embodiment, the method further includes a step of illuminating the linking agent to photochemically attach the linking agent to the surface. In one embodiment, the method further includes a step of providing a plurality of molecules bearing free radical polymerizable groups and illuminating the molecules bearing polymerizable groups and the linking agent to initiate polymerization of the molecules bearing polymerizable groups on the support surface.

In one embodiment the linking agent is used in connection with a plurality of molecules, each bearing one or more polymerizable groups. In accordance with this embodiment, the photoreactive group serves as an initiator to initiate polymerization of the polymerizable groups. As used herein, "polymerizable group" refers to a group that is adapted to be polymerized by initiation via free radical generation, and by photoinitiators activated by visible or long wavelength ultraviolet radiation.

A variety of polymerizable compounds are suitable for use as with the linking agent described herein. In one embodiment, the polymerization products (e.g., a polymer layer resulting from free radical polymerization) is hydrophilic or is capable of being modified to provide hydrophilic characteristics at appropriate reaction conditions (e.g., pH). Moreover, the polymerizable groups of such compounds can include those adapted to participate in free-radical polymerization. In one embodiment, compounds include at least one free-radical polymerizable component (e.g., a vinyl group), and at least one functional group with a high affinity for water. Such functional groups with a high affinity for water can be negatively charged, positively charged, or electrically neutral.

Suitable polymerizable compounds are selected from monomeric polymerizable molecules (e.g., organic monomers), and macromeric polymerizable molecules (e.g., organic macromers). As used herein, "macromer" shall refer to a macromolecular monomer having a molecular weight of about 250 to about 25,000, and from about 1,000 to about 5,000.

Suitable polymerizable compounds can contain electrically neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate).

Alternatively, suitable polymerizable compounds containing electrically neutral hydrophilic functional units include molecules whose polymers, once formed, can be readily modified (e.g., hydrolyzed by the addition of ethylene oxide) to provide products with enhanced affinity for water. Examples of suitable monomers of this type include glycidyl acrylate or methacrylate, whose polymers bear epoxy groups that can be readily hydrolyzed to provide glycol structures having a high affinity for water.

Examples of suitable monomeric polymerizable molecules that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric polymerizable molecules that are negatively charged at appropriate pH levels include molecules whose polymers, once formed, can be readily modified (e.g., by hydrolysis via the addition of ethylene oxide) to provide products with enhanced affinity for water. Examples of suitable monomers of this type include maleic anhydride, whose polymers bear anyhdride groups that can be readily hydrolyzed to provide carboxylic acid groups, or can be readily reacted with amines to provide amide/acid structures with high affinity for water, and polymerized vinyl esters.

Examples of suitable monomeric molecules that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric polymerizable molecules include those molecules that can be readily modified (e.g., by hydrolysis via the addition of ethylene oxide) to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In an alternative embodiment, the polymerizable compounds include macromeric polymerizable molecules. Suitable macromers can be synthesized from monomers such as those illustrated above. According to one embodiment, polymerizable functional components (e.g., vinyl groups) of the macromer can be located at either terminus of the polymer chain, or at one or more points along the polymer chain, in a random or nonrandom structural manner.

The number of free-radical polymerizable groups per molecule can be varied according to the application. For example, a macromer with just one free-radical polymerizable unit can be used. In other instances, however, a macromer with more than one, e.g., two or more polymerizable units per macromer can be used. Additionally, the macromer can contain structural features to provide improved affinity for water in a manner typically unavailable in small molecule structures (e.g., hydrophilic poly(ethylene glycol) materials).

Examples of suitable macromeric polymerizable compounds include methacrylate derivatives, monoacrylate derivatives, and acrylamide derivatives. Macromeric polymerizable compounds include poly(ethylene glycol)monomethyacrylate, methoxypoly(ethylene glycol)monomethacrylate, poly(ethylene glycol)monoacrylate, monomethyacrylamidopoly(acrylamide), poly(acrylamide-co-3-methacrylamidopropylacrylamide), poly(vinylalcohol)monomethacrylate, poly(vinylalcohol)monoacrylate, poly (vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer.

Poly(ethylene glycol) of a desired molecular weight can be synthesized or purchased from a commercial source, and modified (e.g., by reaction with methacrylyl chloride or methacrylic anhydride) to introduce the terminal methacrylate ester units to produce a suitable macromer. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

Polymer Foams

In another embodiment, the linking agent can be used in connection with a composition that is capable of in situ polymerization. In one embodiment, the linking agent can be used in connection with a biocompatible, biodegradable polymer foam. Biodegradable foam used for the treatment of wounds are described, for example, in US Patent Publication No. 2009/0093550, the disclosure of which is hereby incorporated by reference herein in its entirety.

In one embodiment, a biodegradable foam is formed using an "application composition" that includes a polymerizable component, a polymerization initiator, and a gas-releasing component. Suitable polymerization initiators include photoinitiators, including the photoreactive groups of the linking agent described herein. An application composition can be used to form biocompatible foam in situ, or as a pre-formed foam.

The biocompatible polymer foams can be formed from macromers that include polymerizable group(s). A polymerizable group generally includes a carbon-carbon double bond, which can be an ethylenically unsaturated group or a vinyl group. Upon initiation of a polymerization reaction in the application composition, the polymerizable groups, are activated by free radical propagation in the composition, and covalently bonded with other polymerizable groups. As a result of the covalent bonding a crosslinked polymeric matrix is formed. Gas bubbles are generated in the application composition by foaming agents while polymerization of the macromers (which causes polymer matrix formation) is occurring. As a result, a foam is formed, with air pockets (also referred to herein as "cells") partially or completely surrounded by a wall of the crosslinked polymeric matrix.

Examples of polymerizable groups include, but are not limited to, acrylate groups, methacrylate groups, ethacrylate groups, 2-phenyl acrylate groups, acrylamide groups, methacrylamide groups, itaconate groups, and styrene groups. In some aspects the macromers of the invention include one or more methacrylate group(s).

Polymerizable groups can be "pendent" from the macromer at more than one location along the polymer backbone. In some cases the polymerizable groups are randomly located along the length of the polymer backbone. Such randomly spacing typically occurs when the macromer is prepared from a polymer having reactive groups along the length of the polymer, and the polymer is reacted with a limited molar quantity of a compound having the polymerizable group. For example, polysaccharides described herein have hydroxyl groups along the length of the polysaccharide, and a portion of these hydroxyl groups are reacted with a compound having a hydroxyl-reactive group and a polymerizable group.

In other cases one or more polymerizable groups are pendent from the macromer at one or more defined locations along the polymer backbone. For example, a polymer used for the synthesis of the macromer can have a reactive group at its terminus, or reactive groups at its termini. Many polymers prepared from monomers with reactive oxygen-containing groups (such as oxides) have hydroxyl-containing terminal ends which can be reacted with a compound having a hydroxyl-reactive group and a polymerizable group to provide the macromer with polymerizable groups at its termini.

The macromers are based on biocompatible polymers. The term "biocompatible" (which also can be referred to as "tissue compatible") generally refers to the inability of a component, composition, or article to promote a measurably adverse biological response in the body. A biocompatible component, composition, or article can have one or more of the following properties: non-toxic, non-mutagenic, non-allergenic, non-carcinogenic, and/or non-irritating. A biocompatible component, composition, or article, in the least, can be innocuous and tolerated by the body. A biocompatible component, by itself, may also improve one or more functions in the body.

The present invention may be better understood with reference to the following examples. These examples are intended to be representative of specific embodiments of the invention, and are not intended as limiting the scope of the invention.

EXAMPLES

Example 1

Preparation of Photo-PEG-Borate (PPB)

BBE-PEG (20.0 g, 45.0 mmole) is made by a procedure similar to Example 3 of U.S. Pat. No. 6,465,525. The BBE-PEG is placed in a flask with boric acid (0.93 g, 15 mmol) and toluene (100 mL). Water is removed using a Dean Stark trap. Removal of the solvent gives a residue of the PPB.

Example 2

Preparation of Photo-PEG-Borate Amine Complex (PPB-AC)

PPB (10.0 g, 7.2 mmole; from example 1 above) is dissolved in toluene (100 mL). A Dean Stark trap is used to insure a dry solution. Diethanol amine (0.76 g, 7.2 mmol) is added to the PPB solution. Evaporation of the solvent gives the PPB-AC product.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A compound having the structure:

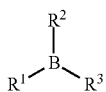

wherein
R¹ and R² are each radicals comprising a photoreactive group; and
R³ is selected from OH, a radical comprising a photoreactive group an alkyl group and an aryl group.

2. The compound of claim 1, the photoreactive groups comprising an aryl ketone.

3. The compound of claim 1, the photoreactive groups comprising benzophenone.

4. The compound of claim 1, wherein R³ is a radical comprising a photoreactive group.

5. The compound of claim 1, wherein R¹ is a radical comprising a photoreactive group and a subunit having structure —[X]$_m$—, wherein X is selected from $CH_2$, $OCH_2CH_2$, and $OCH_2CH_2CH_2$; and m is from 1-20.

6. The compound of claim 1, the compound having the structure:

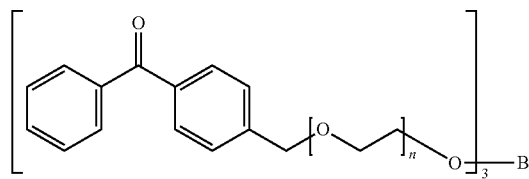

wherein n is from 1-20.

7. The compound of claim 1, further complexed with an amine.